(12) United States Patent
Lin et al.

(10) Patent No.: US 10,346,665 B2
(45) Date of Patent: *Jul. 9, 2019

(54) NOISE REDUCED CAPACITIVE IMAGE SENSOR AND METHOD OPERATING THE SAME

(71) Applicant: SunASIC Technologies Limited, Wanchai (HK)

(72) Inventors: Chi Chou Lin, New Taipei (TW); Zheng Ping He, Taipei (TW)

(73) Assignee: SUNASIC TECHNOLOGIES LIMITED, Wanchai (HK)

( * ) Notice: Subject to any disclaimer, the term of this patent is extended or adjusted under 35 U.S.C. 154(b) by 154 days.

This patent is subject to a terminal disclaimer.

(21) Appl. No.: 15/607,703

(22) Filed: May 30, 2017

(65) Prior Publication Data

US 2018/0349662 A1 Dec. 6, 2018

(51) Int. Cl.
*G06K 9/00* (2006.01)
*G06K 9/40* (2006.01)
*A61B 5/1172* (2016.01)
*G06F 3/044* (2006.01)
*G06F 3/041* (2006.01)
*A61B 5/00* (2006.01)
*A61B 5/0428* (2006.01)

(52) U.S. Cl.
CPC ......... *G06K 9/0002* (2013.01); *A61B 5/1172* (2013.01); *A61B 5/7225* (2013.01); *G06F 3/044* (2013.01); *G06F 3/0416* (2013.01); *G06K 9/40* (2013.01); *A61B 5/04284* (2013.01); *A61B 2562/0214* (2013.01); *A61B 2562/046* (2013.01); *G06F 2203/04103* (2013.01)

(58) Field of Classification Search
CPC .................................................. G06K 9/0002
See application file for complete search history.

(56) References Cited

U.S. PATENT DOCUMENTS

| 3,497,824 | A | * | 2/1970 | Goordman | H03F 3/45085 330/258 |
| 8,164,652 | B2 | * | 4/2012 | Kimura | H04N 5/374 348/230.1 |
| 9,600,707 | B1 | * | 3/2017 | Ramberg | G06F 3/045 |
| 2005/0005703 | A1 | * | 1/2005 | Saito | G01L 9/12 73/780 |

(Continued)

Primary Examiner — Utpal D Shah
(74) Attorney, Agent, or Firm — Jackson IPG PLLC; Demian K. Jackson

(57) ABSTRACT

A noised-reduced capacitive image sensor and a method operating the capacitive image sensor are provided. The capacitive image sensor includes: a number of capacitive sensing units forming an array, each capacitive sensing unit for transforming a distance between a portion of a surface of an approaching finger and a top surface thereof into an output electric potential, wherein a value of the output electric potential is changed by a driving signal applied to the sensing unit; at least one sample-and-hold circuit for capturing and retaining different output electric potentials; at least one signal conditioning circuit, each comprising at least one differential amplifier for amplifying a difference between two electric potentials retained by the sample-and-hold circuit; and a driving source, for providing the driving signal to the capacitive sensing units.

11 Claims, 9 Drawing Sheets

(56) References Cited

U.S. PATENT DOCUMENTS

| | | | |
|---|---|---|---|
| 2005/0024065 A1* | 2/2005 | Umeda | G01D 5/2417 |
| | | | 324/663 |
| 2005/0141263 A1* | 6/2005 | Umeda | G06K 9/0002 |
| | | | 365/149 |
| 2016/0110581 A1* | 4/2016 | Heo | G06K 9/0002 |
| | | | 382/124 |
| 2016/0180619 A1* | 6/2016 | Riedijk | G07C 9/00158 |
| | | | 324/679 |
| 2016/0232394 A1* | 8/2016 | Riedijk | G06F 3/044 |
| 2016/0307021 A1* | 10/2016 | Kim | G06K 9/0002 |
| 2017/0091509 A1* | 3/2017 | Riedijk | G06K 9/22 |
| 2017/0103246 A1* | 4/2017 | Pi | G06K 9/0002 |
| 2018/0144171 A1* | 5/2018 | Liang | H03K 17/9622 |

\* cited by examiner

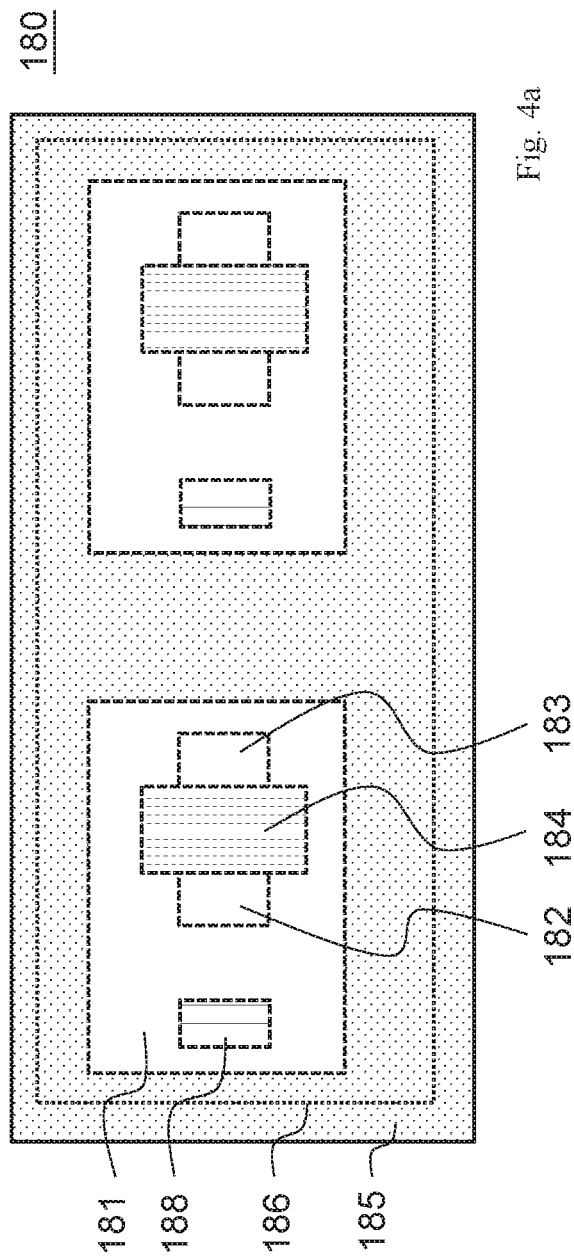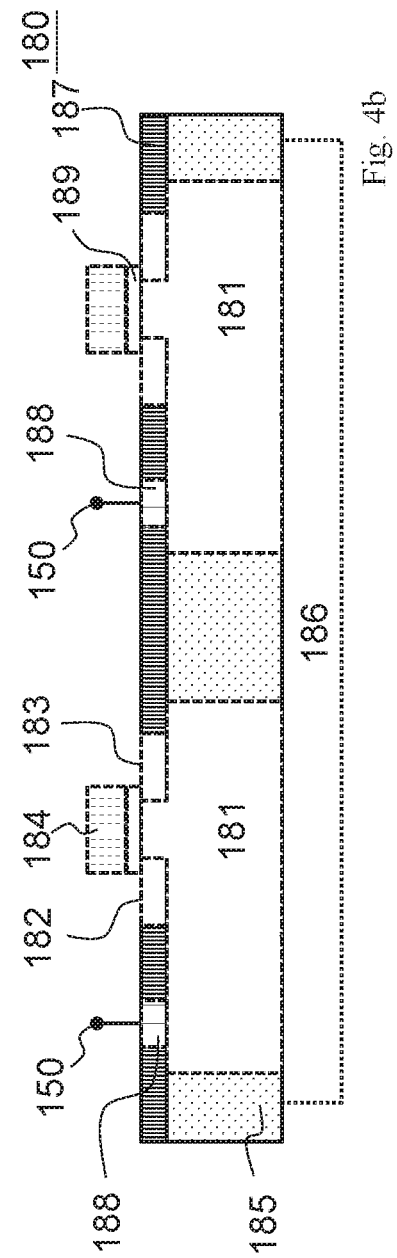

NOISE REDUCED CAPACITIVE IMAGE SENSOR AND METHOD OPERATING THE SAME

FIELD OF THE INVENTION

The present invention relates to a capacitive image sensor and a method to operate the capacitive image sensor. More particularly, the present invention relates to a capacitive image sensor with noise reduction feature and a method to operate the capacitive image sensor.

BACKGROUND OF THE INVENTION

There are many human physiological characteristics which can be used to provide personnel identification for security purposes, such as fingerprint, retina, iris, DNA, or even face features. For all the devices that are capable of distinguishing some physiological characteristics of one person from others', a fingerprint reader has the lowest cost and complexity, while the identification results are generally pretty good. In addition, the size of data required to store the minutiae of one fingerprint is small (ranging from 120 bytes to 2K bytes). This makes fingerprint identification devices widely accepted in many applications.

There are also many types of sensing techniques for capturing fingerprints. The popular ones are the optical type and capacitive type. Optical fingerprint sensing modules utilize reflected light intensity from the surface of a finger to tell where the ridges and valleys are on the contact portion of the finger. The advantage of the optical technique is reliability and low cost. However, due to the size of the embedded optical lens, the form factor of an optical fingerprint sensing module cannot be kept small. It is difficult for the optical type sensor to be embedded in portable devices. The capacitive-type fingerprint identification modules, on the other hand, are made out of silicon chips and can be made very compact. In some cases, when a fingerprint image can be fetched by slide scanning, the fingerprint sensor can be even thin and slim, too. The small form factor of capacitive-type fingerprint identification module makes it suitable for portable applications such as access control badges, bank cards, cellular phones, tablet computers, USB dongles, etc.

Capacitive-type fingerprint sensors are based on the principle that the capacitance of two parallel conductive plates is inversely proportional to the distance between them. A capacitive fingerprint sensor consists of an array of sensing units. Each sensing unit contains a sensing plate. By using the sensing plate as one plate of the two-plated capacitor and a dermal tissue as another plate, ridges and valleys of a fingerprint can be located by measuring the different capacitances. There are many prior arts related to the capacitive-type fingerprint identification module. Most of them have been applied to manufacture fingerprint sensors. However, there are also many problems pending for solutions. One of them is the accuracy of the sensing elements.

Due to the high-density nature, the popular capacitive fingerprint sensors are mainly manufactured with semiconductor processes. The precision of the sensing elements is affected by many factors inherited in the manufacturing technology, such as density of chemical impurities, alignment of photomasks, equipment control, etc., whose uncertainty or variation will be reflected in the different behavior between devices, or even a fixed pattern noise seen in the captured fingerprint images of the same device. In order to achieve the best performance of personal identification, it is desirable to improve the quality of the captured fingerprint image by reducing the noise pattern. A common practice to eliminate fixed pattern noise is to calibrate the device before use. The calibration data can be calculated and stored as part of the manufacturing process, or right before the device is used. However, in either case, a certain amount of memory storage space must be set aside for the calibration data, and this storage space will increase the system cost. Therefore, an innovative pixel sensing element, a capacitive fingerprint sensor made by the pixel sensing elements and a method for running the pixel sensing element are desirable.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

In order to settle the issues mentioned above, a capacitive image sensor is disclosed. The capacitive image sensor includes: a number of capacitive sensing units forming an array, each capacitive sensing unit for transforming a distance between a portion of a surface of an approaching finger and a top surface thereof into an output electric potential, wherein a value of the output electric potential is changed by a driving signal applied to the sensing unit; at least one sample-and-hold circuit for capturing and retaining different output electric potentials; at least one signal conditioning circuit, each comprising at least one differential amplifier for amplifying a difference between two electric potentials retained by the sample-and-hold circuit; and a driving source, for providing the driving signal to the capacitive sensing units. The driving signal is a potential change or potential changes, caused by a positive waveform and/or a negative waveform provided by the driving source. The electric potential at each part of the capacitive sensing units is set to a constant value during reset stages. The difference between two output electric potentials retained in the sample-and-hold circuit is a noise-reduced value representing a distance between the capacitive sensing unit and the portion surface of the finger above the capacitive sensing unit. The sample-and-hold circuit retains at least a first and a second output electric potentials under a corresponding positive waveform or negative waveform. The capacitive image sensor sequentially collects the noise-reduced values under the corresponding positive waveform and negative waveform for each pixel (capacitive sensing unit), and maps the noise-reduced values to corresponding locations of the capacitive sensing units to obtain a noise-reduced image of the finger.

Preferably, shapes of the positive waveform and the negative waveform may be symmetric. The positive waveform or the negative waveform may be a step function. The at least one signal conditioning circuit may further include an analog-to-digital converter for converting the output electric potentials from the differential amplifier into a digitized value.

According to the present invention, the capacitive sensing unit may further include: a sensing electrode; a voltage follower, wherein an input node of the voltage follower is connected to the sensing electrode, and an output node of the voltage follower is connected to the sample-and-hold circuit; a comparative capacitor, wherein one node of the comparative capacitor is electrically connected to the voltage follower, and the other node thereof is electrically connected to the driving source; and a bias voltage supply circuit, for providing different bias voltages to the sensing electrode. The comparative capacitor, a portion of the bias voltage supply circuit, and the voltage follower are MOS devices formed in an isolated well.

The isolated well may utilize deep n-well (DNW) implanted structure. The comparative capacitor may include a reference capacitor and parasitic capacitance. The reference capacitor may be a MOSFET (Metal-Oxide-Semiconductor Field-Effect Transistor) capacitor, a PIP (Polysilicon-Insulator-Polysilicon) capacitor or a MIM (Metal-Insulator-Metal) capacitor. The capacitive image sensor may further include a control and IO circuit for handling timing sequence and data input/output of the capacitive image sensor.

The sample-and-hold circuit may further include: two charge holding capacitors, for holding the output electric potentials sent by the voltage follower; and at least one selecting switch, for switching between the charge holding capacitors.

The present invention also discloses a method for operating a capacitive image sensor to reduce noise. The method includes the steps of: during a first sensing stage, providing a first measurement to the sample-and-hold circuit while a first input waveform is provided by the driving source; during a second sensing stage, providing a second measurement to the sample-and-hold circuit while a second input waveform is provided by the driving source; during an output stage, the output signal is given by the differential amplifier according to the difference between the first and the second measurements; sequentially collecting the noise-reduced values obtained under corresponding positive waveform and negative waveform for each pixel; converting the noise-reduced values into digitized noise-reduced values; and mapping the digitized noise-reduced values to corresponding locations of capacitive sensing units. If the first waveform is a positive waveform, then the second waveform is a negative waveform; if the first waveform is a negative waveform, then the second waveform is a positive waveform.

BRIEF DESCRIPTION OF THE DRAWINGS

FIG. 4a is a perspective view of the physical structure of two isolated wells of NMOS transistors, and FIG. 4b is a side view of the isolated wells.

DETAILED DESCRIPTION OF THE PREFERRED EMBODIMENTS

The present invention will now be described more specifically with reference to the following embodiments.

Figure 1:
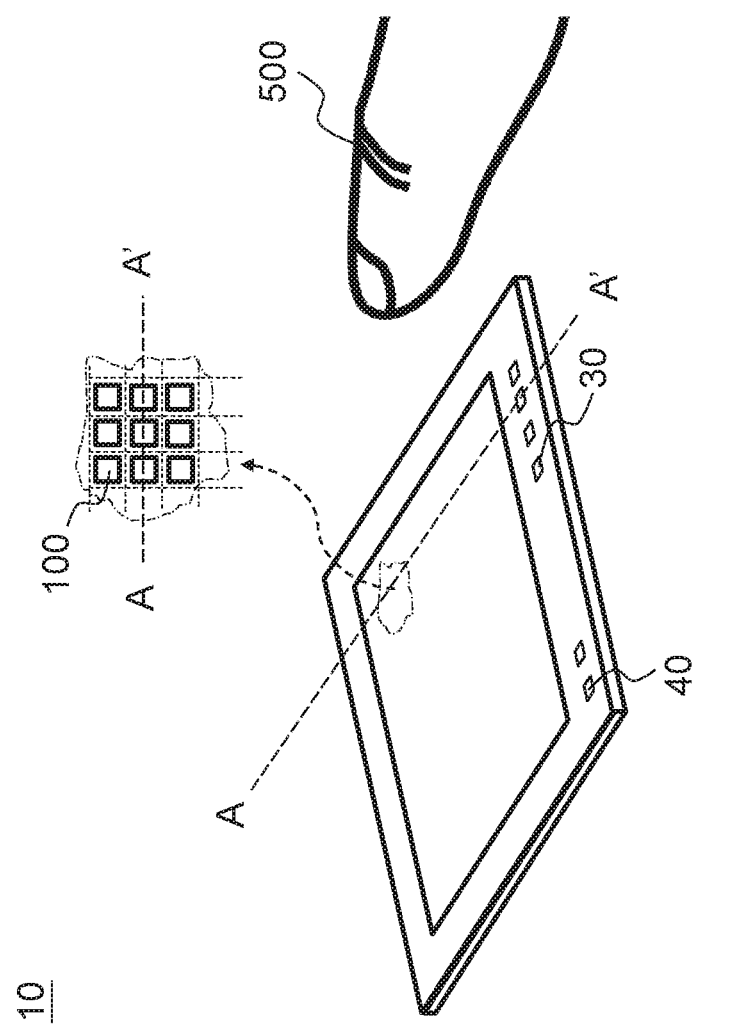
FIG. 1 is a schematic diagram of a capacitive image sensor according to the present invention.

Please see FIG. 1. FIG. 1 shows a schematic diagram of a capacitive image sensor 10 (chip) according to the present invention. The capacitive image sensor 10 is used to depict ridges and valleys of a surface of a finger 500, further converting the results into a noise-reduced image of the fingerprint. The capacitive image sensor 10 includes an array of capacitive sensing units 100, contact pads 40 of a power supply, and contact pads 30 of an input/output (I/O) interface. The output from each capacitive sensing unit 100 represents one corresponding pixel of the fingerprint image.

Figure 2:
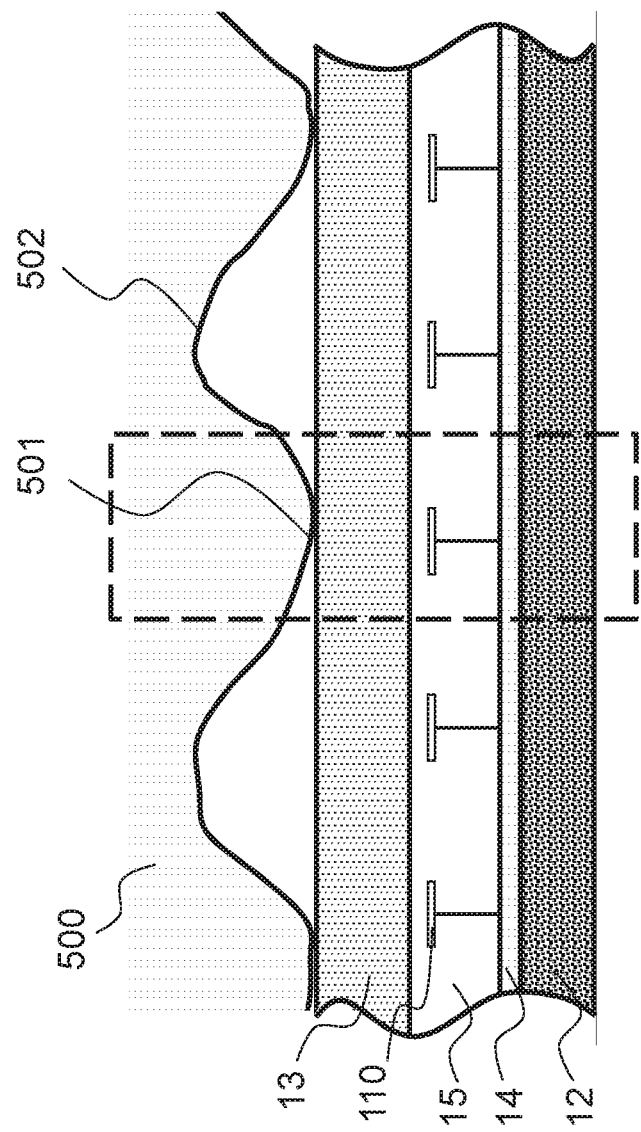
FIG. 2 is a schematic cross-section of a portion of the capacitive image sensor taken along line A-A' in FIG. 1.

FIG. 2 is a schematic cross-section of a portion of the capacitive image sensor 10 taken along line A-A' in FIG. 1, with a protective layer 13 located on top capacitive image sensor 10 and a fingertip 500 placed on the protective layer 13. The protective layer 13 may be made of glass, sapphire, epoxy compound, or coating material. The capacitive image sensor 10 includes a semiconductor substrate 12, having the array of capacitive sensing units 100 formed thereon. The surface of the fingertip 500 includes ridges 501 that are in contact with the protective layer 13 and valleys 502 that are spaced apart from the protective layer 13. Each capacitive sensing unit 100 can be used to transform a distance between a portion of a surface of the approaching finger 500 and a top surface of itself into an output electric potential. Five capacitive sensing units 100 are shown in FIG. 2, and one of the capacitive sensing units 100 is enclosed by a dashed frame. Each capacitive sensing unit 100 includes a sensing electrode 110 in the form of a conductive plate. Below the conductive plate are active semiconductor circuitries 14 schematically shown by a forward-diagonal-lines region in FIG. 2. At least one insulating layer 15 is formed to enclose the sensing electrodes 110. Details of the active semiconductor circuitry 14 will be described in later paragraphs.

Figure 3:
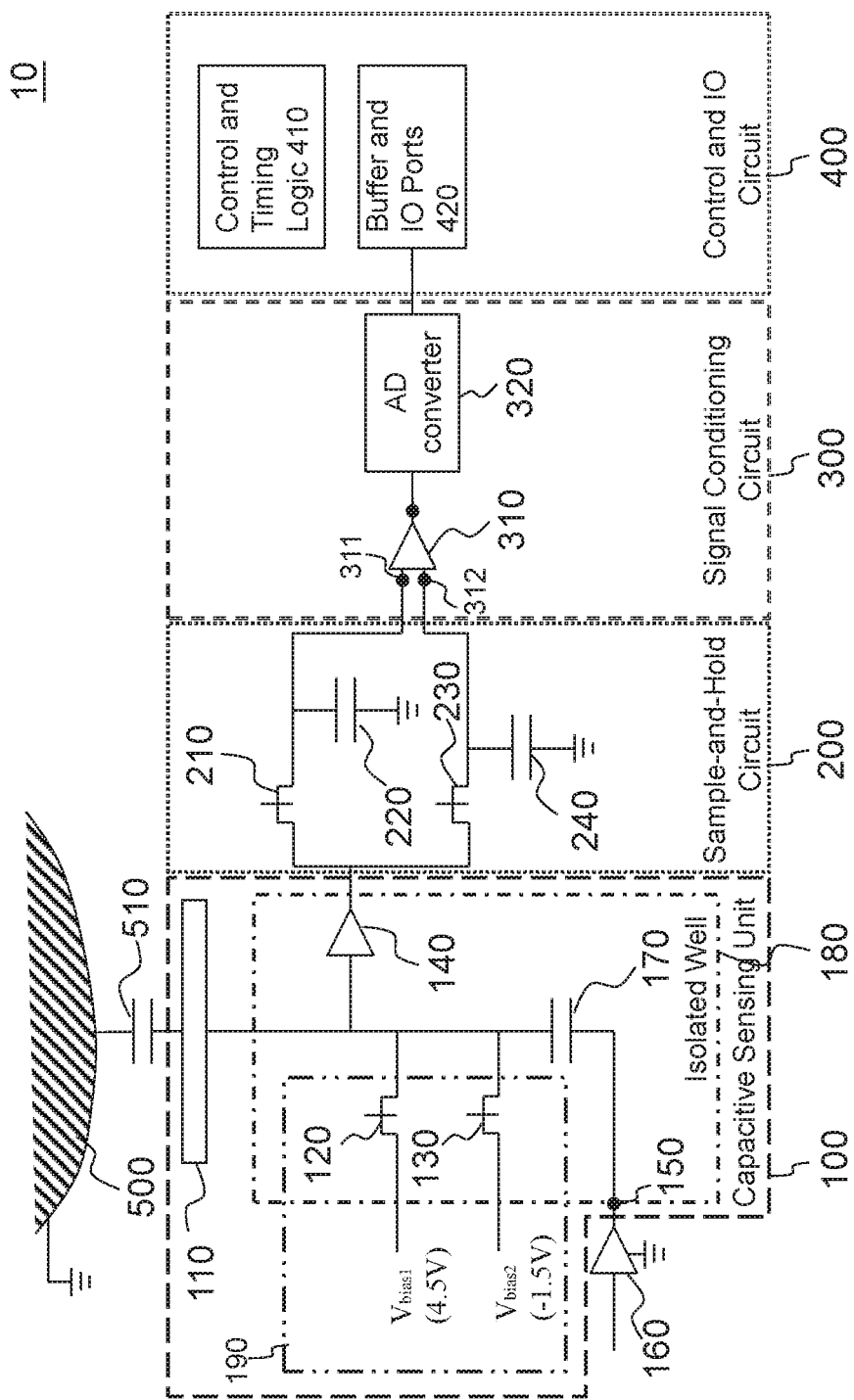
FIG. 3 is an equivalent circuit of a capacitive image sensor (one pixel) of a first embodiment according to the present invention.

Please refer to FIG. 3, FIG. 3 is an equivalent circuit of the capacitive image sensor 10 (one pixel) according to the present invention. The capacitive image sensor 10 includes an array of capacitive sensing units 100 (enclosed by dashed lines), a number of driving sources 160, a number of sample-and-hold circuits 200 (enclosed by dotted lines), a number of signal conditioning circuits 300 (enclosed by double-dashed lines), and a control and IO circuit 400 (enclosed by double-dotted lines). Each circuit will be described in detail below. In order to have a better understanding, only one capacitive sensing unit 100, one sample-and-hold circuit 200 and one signal conditioning circuit 300 are used for illustration.

The capacitive sensing unit 100 is a combination of circuit and metal/insulator structure built to detect small capacitance change to produce a corresponding voltage output. The capacitive sensing unit 100 includes an isolated well 180, a sensing electrode 110, a first bias switch 120, a second bias switch 130, a voltage follower 140, a well contact 150, and a comparative capacitor 170. A parasitic capacitance (not shown) representing the sum of stray capacitance between the sensing electrode 110 and other parts (not shown) of the capacitive sensing unit 100 that are not connected to the sensing electrode 110 can be treated as a part of the comparative capacitor 170. The value of the parasitic capacitance, denoted as $C_p$, may include the parasitic input capacitance of the voltage follower 140, the drain-to-body capacitance of the first bias switch 120 and/or the second bias switch 130, or the stray capacitance of any device with one node connected to the sensing electrode 110. A reference capacitor (not shown), having a capacitance $C_r$, is formed between the driving source 160 and the sensing electrode 110, and the reference capacitor is used to inject driving signals to the sensing electrode 110. The reference capacitor is a MOSFET (Metal-Oxide-Semiconductor Field-Effect Transistor) capacitor, a PIP (Polysilicon-Insulator-Polysilicon) capacitor or a MIM (Metal-Insulator-Metal) capacitor. The comparative capacitor 170 is an equivalent capacitor, denoted as $C_c$, representing the total effect of the parasitic capacitance and the reference capacitor, i.e. $C_c=C_r+C_p$. When a finger 500 approaches the capacitive sensing unit 100, a finger capacitance 510, denoted as $C_f$, is formed therebetween. The sensing electrode 110 is a metal plate at the top side of the capacitive sensing unit 100, used to form one side of a parallel plate capacitor. Here, the parallel plate capacitor is an equivalent capacitor representing the finger capacitance 510. The other side of the parallel plate capacitor is the surface of the finger 500, which is part of the human body. The human body is considered as part of earth ground, or connected to earth ground through a low impedance path. The first bias switch 120 is a MOS device used as a switch to connect or disconnect a first bias voltage, denoted as $V_{bias1}$, to the sensing electrode 110. The first bias voltage is a 4.5V constant voltage reference in the present embodiment. The second bias switch 120 is another MOS device used as a switch to connect or disconnect a second bias voltage, denoted as $V_{bias2}$, to the sensing electrode 110. The second bias voltage is a −1.5V constant voltage reference in the present embodiment. The voltage follower 140 is a circuit device that has input and output signal. The output signal tracks the input signal. Usually, a voltage follower is implemented as a unity gain amplifier. The input node of the voltage follower 140 is connected to the sensing electrode 110. The driving source 160 is a low-impedance voltage source to provide a multi-level waveform as the driving signal. More precisely, the driving signal is a potential change or potential changes, caused by a positive waveform and/or a negative waveform provided by the driving source 160. The first bias switch 120, the second bias switch 130, the voltage follower 140, and the comparative capacitor 170 are all formed inside the isolated well 180 (enclosed by a dot-dash frame). The well contact 150 is a contact node for maintaining a well potential of the isolated well 180, and is connected to the output node of the driving source 160. Every node connected to the well contact 150 has the same potential as the well potential. Therefore, the components inside the isolated well 180 have their ground potential refer to the well potential. The well potential equals to the output voltage of the driving source 160. The change of the well potential following the injected driving signal then causes charge redistribution in the capacitive sensing unit 100 through the comparative capacitor 170, and further changes the electric potential at the sensing electrode 110. Multiple capacitive sensing units 100 may share one driving source 160, e.g. well contacts of one column of the capacitive sensing units 100 may connect to one driving source. A bias voltage supply circuit 190 (enclosed by a dot-dot-dash frame) is a collective name for the components that control the supplying of the bias voltage to the sensing electrode 110. The bias voltage supply circuit 190 comprising the first bias switch 120 and the second bias switch 130 in the present embodiment. The purpose of the bias voltage supply circuit 190 is to provide different bias voltages to the sensing electrode 110 at different times.

Please refer to FIG. 4a and FIG. 4b. FIG. 4a is a perspective view of the physical structure of two isolated wells of NMOS transistors, and FIG. 4b is a side view of the isolated wells. The isolated well 180 includes an isolated P-type implant area (isolated P-well) 181, two heavily doped n-type regions that act as a source 182 and a drain 183, a gate node 184, an N-type implant area (N-well) 185, a layer of deep N-type implant area (DNW) 186, an isolated layer 187, a bulk contact (B-bulk) 188 to the bulk (the P-type implant area 181), and a thin isolator layer (gate oxide) 189. The source 182, the drain 183, the gate node 184, the bulk contact 188, and the thin isolator layer 189 are parts of the well-known structure of an ordinary NMOS transistor. However, to make the P-well isolated, other parts of the structure are needed. The isolated well 180 is a MOS implant structure to allow the bulk contact 188 of a transistor to be isolated and driven by a changing signal. For a P-type substrate wafer, the isolated well 180 for an NMOS transistor can be constructed as a P-type implant area (isolated P-well) 181 surrounded by a ring of N-well 185 and a layer of DNW 186 (deep N-well) from below, which are connected to a constant voltage (not shown) that is higher than the potential of the signal driving the isolated P-well 181. The bulk contact 188 is further connected to the well contact 150 for receiving the signal from driving source 160. In other words, the isolated well 180 is configured in such a way that a current can be prevented from flowing in/out from the interface between the P-type implant area 181 and the deep N-type implant area (DNW) 186, or from that between the P-type implant area 181 and the N-type implant area (N-well) 185. In another embodiment, the N-type implant area (N-well) 185 can be replaced by any method and materials, e.g. shallow trench isolation (STI) and/or deep trench isolation, that prevent current leakage at the interface between that area and the P-type implant area 181.

The sample-and-hold circuit 200 in FIG. 3 is a device used to capture and retain input voltage signals. The sample-and-hold circuit 200 includes a first sample switch 210, a first charge holding capacitor 220, a second sample switch 230, and a second charge holding capacitor 240. The first sample switch 210 is formed between the output node of the voltage follower 140 and the first charge holding capacitor 220, and is a MOS device used as a switch to connect the output of the voltage follower 140 to the first charge holding capacitor 220. The first charge holding capacitor 220 is a capacitor used to capture and retain a first output electric potential, denoted as $V_1$, from the voltage follower 140 through the first sample switch 210. One node of the first charge holding capacitor 220 is connected to the first sample switch 210 and the other node is connected to the ground. The second sample switch 230 is formed between the output node of the voltage follower 140 and the second charge holding capacitor 240, and is a MOS device used as a switch to connect the output of the voltage follower 140 to the second charge holding capacitor 240. The second charge holding capacitor 240 is a capacitor used to capture and retain a second output electric potential, denoted as $V_2$, from the voltage follower 140 through the second sample switch 230. One node of the second charge holding capacitor 240 is connected to the second sample switch 230 and the other node is connected to the ground. The first sample switch 210 and the second sample switch 230 work together as a selecting switch for choosing the output target (either the first or the second charge holding capacitor) for the voltage follower 140. In the present embodiment, the sample-andhold circuit 200 retains at least a first and a second output electric potentials under a corresponding positive waveform or negative waveform.

The signal conditioning circuit 300 is a circuit to amplify a voltage difference between the first and second output electric potentials, possibly with level shift, and then convert the result to a digitized value. The signal conditioning circuit 300 comprises a differential amplifier 310 and an analog-to-digital converter (AD converter) 320. A first input node 311 of the differential amplifier 310 is connected to the first charge holding capacitor 220 and the first sample switch 210, a second input node 312 of the differential amplifier 310 is connected to the second charge holding capacitor 240 and the second sample switch 230, and an output node of the differential amplifier 310 is connected to an input node of the analog-to-digital converter 320. The differential amplifier 310 is an amplifier used to produce a voltage output that is proportional to the difference between the first and second output electric potentials. The analog-to-digital converter 320 converts the output electric potential of the differential amplifier 310 and produces a binary value that represents the voltage level.

The Control and IO circuit 400 is a circuit that handles the timing sequence and data input/output of the capacitive image sensor 10. The Control and IO circuit 400 comprises a Control and Timing logic 410 and Buffer and IO ports 420. The Control and Timing logic 410 controls all switches in the capacitive image sensor 10. The Buffer and IO ports 420 receives the output data of the analog-to-digital converter 320 and store the data into a buffer and then send out the data at a proper time.

Figure 5:
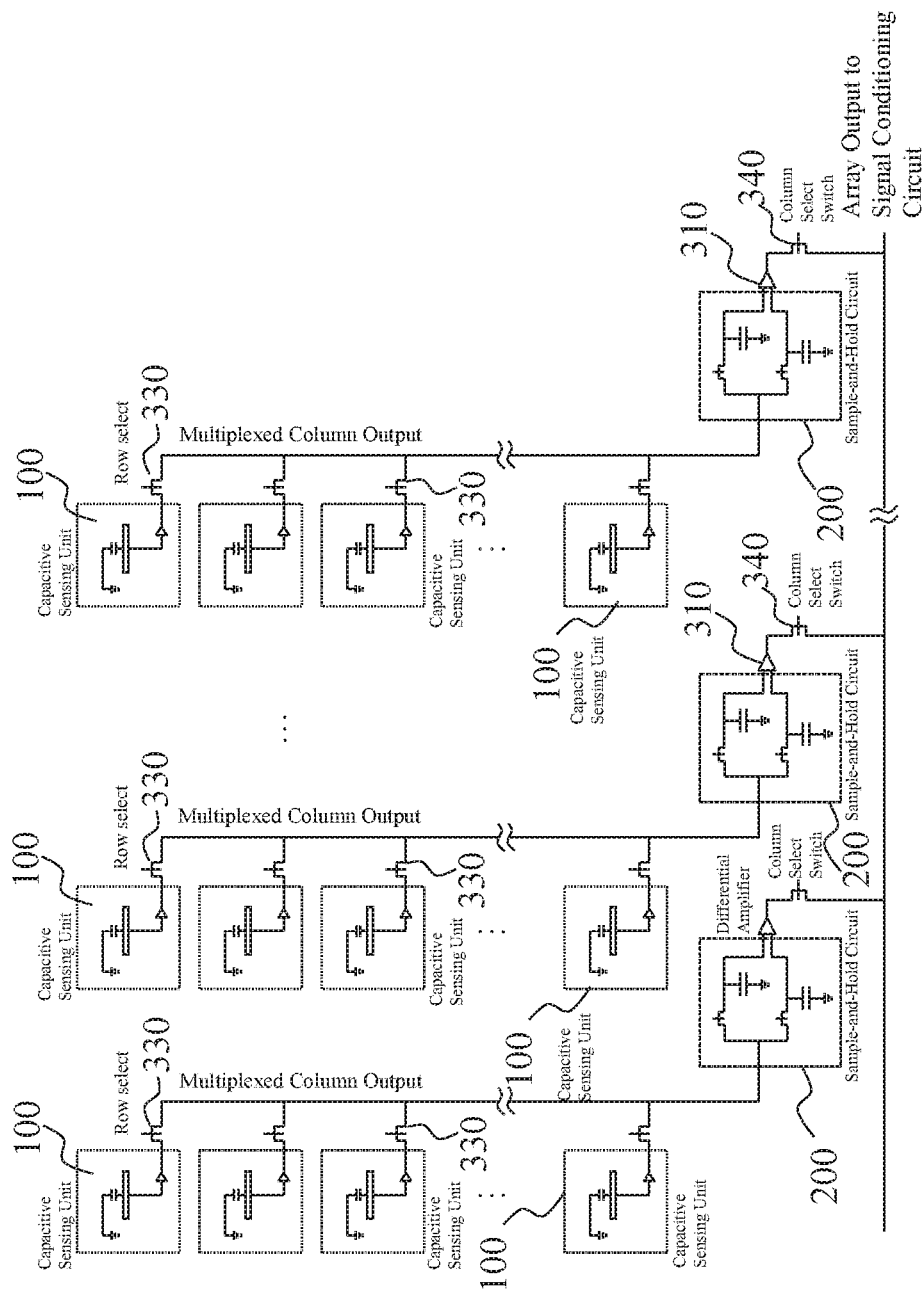
FIG. 5 a schematic diagram of a typical implementation of the capacitive image sensor according to the present invention.

Please refer to FIG. 5. FIG. 5 is a schematic diagram of a typical implementation of the capacitive image sensor 10 according to the present invention. The capacitive image sensor 10 comprises a two-dimensional array of capacitive sensing units 100 and a number of sample-and-hold circuits 200. Other circuits are not shown in this diagram. The two-dimensional array of the capacitive sensing units 100 is enabled in a row-by-row sequence. The capacitive sensing units 100 in the same column share the same output wire through separate row select signals. One row is enabled by the corresponding row select signal at a time. The row select switches 330 are controlled by the row select signals sent out by the control and timing logic 410. Each column output wire connects to a shared sample-and-hold circuit 200 and a differential amplifier 310. The output of the differential amplifiers 310 is multiplexed to a single output signal through a set of column select signals. The column select switches 340 are controlled by column select signals sent out by the control and timing logic 410. Only one of the column select signals is activated at a time, to allow the output of the differential amplifiers 310 to be sequentially delivered to the analog-to-digital converter 320 in the signal conditioning circuit 300.

Figure 6:
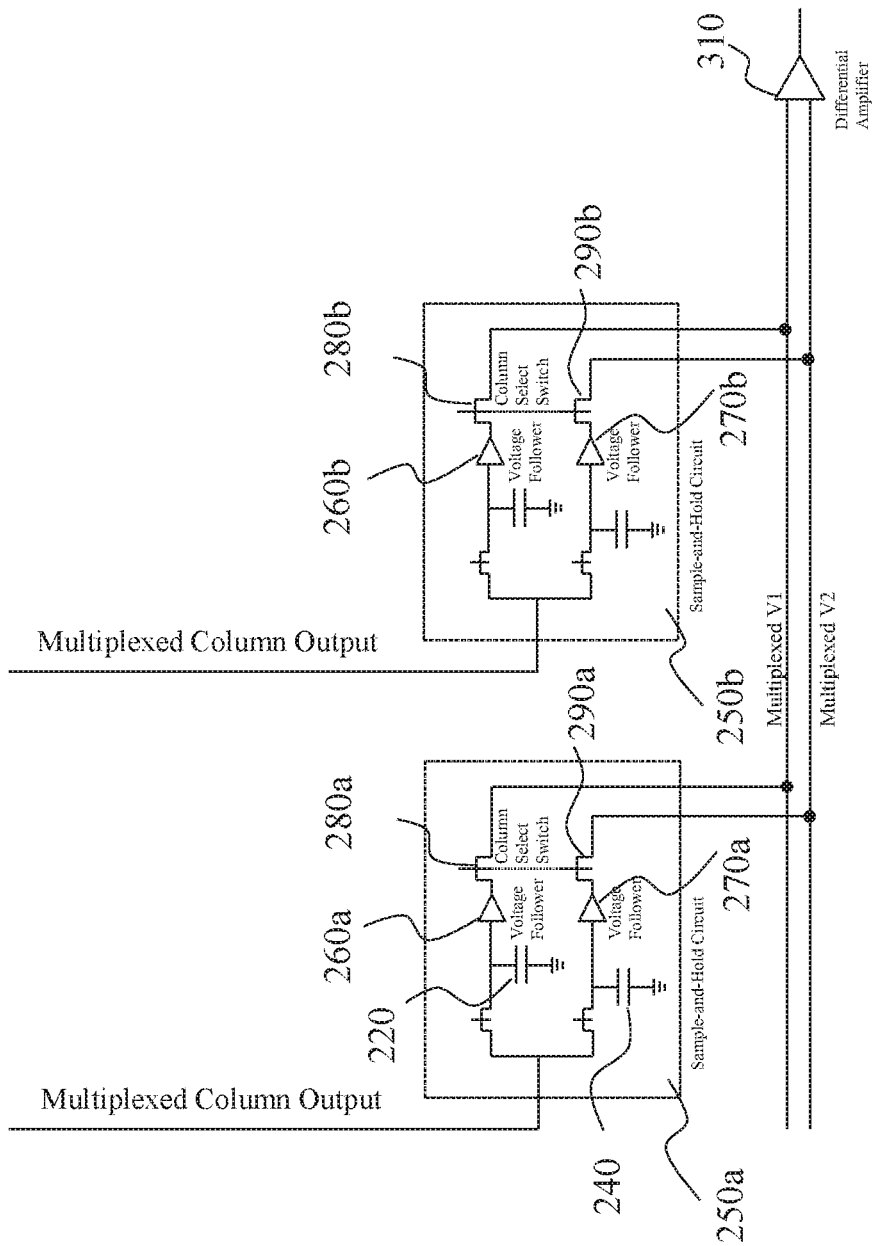
FIG. 6 shows an alternative structure of a sample-and-hold circuit and that of the connection between the differential amplifier and the sample-and-hold circuit.

Please refer to FIG. 6. FIG. 6 shows an alternative structure of a sample-and-hold circuit 250a/250b and that of the connection between the differential amplifier 310 and the sample-and-hold circuit 250. The sample-and-hold circuits 250a/250b may share the same differential amplifier 310 through additional voltage followers (e.g. 260a and 270a), and column select switches (e.g. 280a and 290a) between the charge holding capacitors (220 and 240) and the differential amplifier 310. For example, a voltage follower 260a and a column select switch 280a are formed between the first charge holding capacitor 220 and the differential amplifier 310, and a voltage follower 270a and a column select switch 290a are formed between the second charge holding capacitor 240 and the differential amplifier 310.

Figure 7:
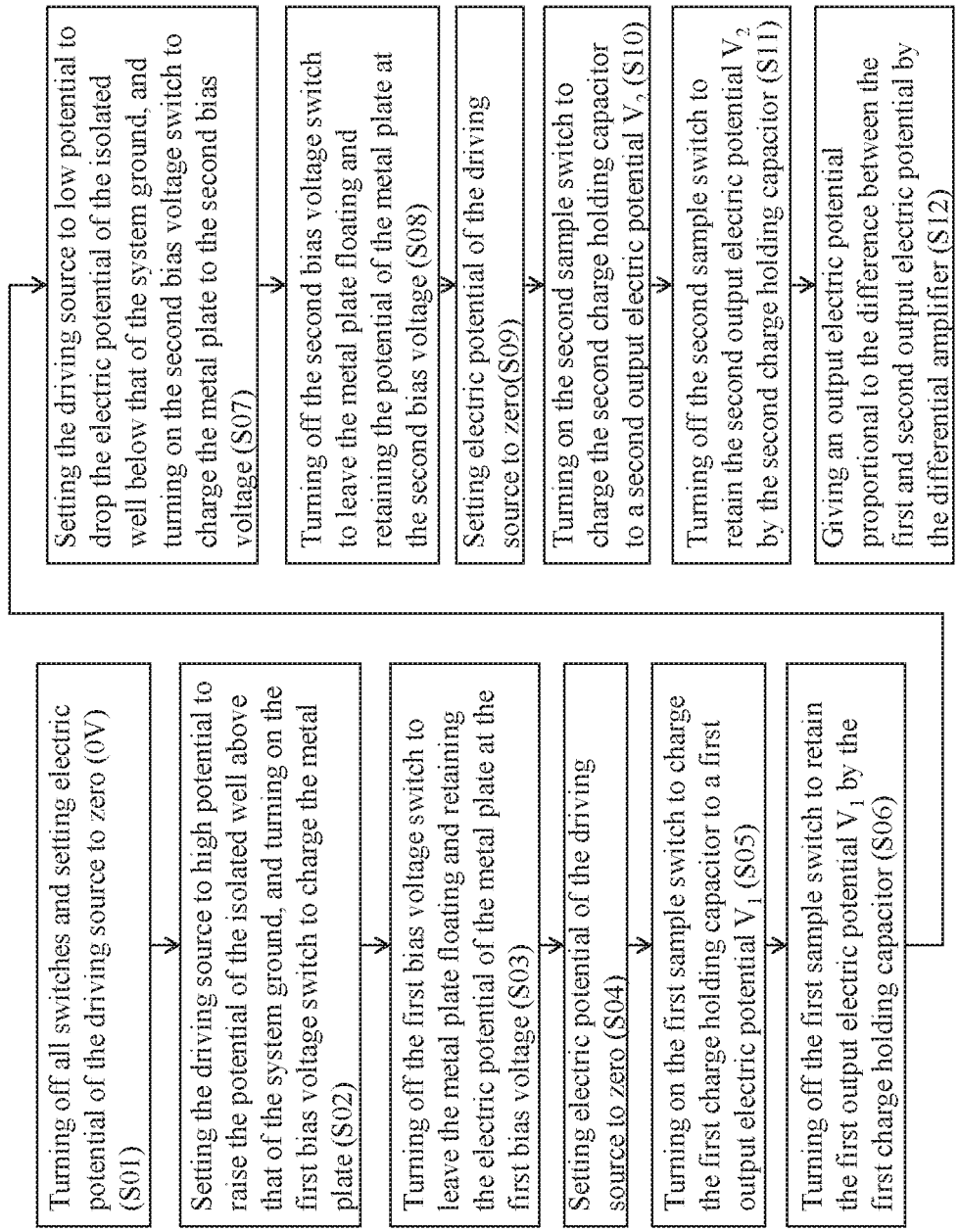
FIG. 7 is a flowchart illustrating a procedure to operate a capacitive sensing unit in the capacitive image sensor of the first embodiment.

A method for operating the capacitive image sensor 10 is also disclosed. Please refer to FIG. 7. It is a flowchart illustrating a procedure to operate a capacitive sensing unit 100 in the capacitive image sensor 10. The steps are:

(S01) turning off all switches (the first bias voltage switch 120, the second bias voltage switch 130, the first sample switch 210, and the second sample switch 230) and setting the electric potential of the driving source to zero (0V);

(S02) setting the driving source 160 to high potential (3V) to raise the potential of the isolated well 180 above that of the system ground, and turning on the first bias voltage switch 120 to charge the sensing electrode 110 to the first bias voltage (4.5V);

(S03) turning off the first bias voltage switch 120 to leave the sensing electrode 110 floating and retaining the electric potential of the sensing electrode 110 at the first bias voltage (4.5V);

(S04) setting the electric potential of the driving source 160 to zero (0V);

(S05) turning on the first sample switch 210 to charge the first charge holding capacitor 220 to a first output electric potential $V_1$ that tracks the electric potential of the sensing electrode 110;

(S06) turning off the first sample switch 210 to retain the first output electric potential $V_1$ by the first charge holding capacitor 220;

(S07) setting the driving source 160 to low potential (−3V) to drop the electric potential of the isolated well 180 below that of the system ground, and turning on the second bias voltage switch 130 to charge the sensing electrode 110 to the second bias voltage (−1.5V);

(S08) turning off the second bias voltage switch 130 to leave the sensing electrode 110 floating and retaining the potential of the sensing electrode 110 at the second bias voltage (−1.5V);

(S09) setting the electric potential of the driving source 160 to zero (0V);

(S10) turning on the second sample switch 230 to charge the second charge holding capacitor 240 to a second output electric potential $V_2$ that tracks the potential of the sensing electrode 110.

(S11) turning off the second sample switch 230 to retain the second output electric potential $V_2$ by the second charge holding capacitor 240; and (S12) giving an output electric potential proportional to the difference between the first and second output electric potential by the differential amplifier 310.

Here, steps S02 and S03 (S02-S03) are the first reset stage, steps S04 to S06 (S04-S06) are the first sensing stage, steps S07 to S08 (S07-S08) are the second reset stage, steps S09 to S11 (S09-S11) are the second sensing stage, and step S12 is the output stage. The output electric potential proportional to the difference between the first and second output electric potential in step S12 is a noise-reduced value of that pixel (capacitive sensing unit). The noise-reduced value represents a distance between the capacitive sensing unit and the portion surface of the finger above the capacitive sensing unit. The sequence of steps S02-S06 and steps S07-S11 can be exchanged. Namely, a positive waveform and a negative waveform are applied by the driving source to get the noise-reduced value no matter what the sequence is. For a better understanding, take the waveform formed from step S02 to step S04 as a first waveform and the waveform formed from step S07 to step S09 as a second waveform. If the first waveform is a positive waveform, then the second waveform is a negative waveform; if the first waveform is a negative waveform, then the second waveform is a positive waveform. There may be additional steps to convert the output electric potentials into a digitized image. The steps are:

(S13) sequentially collecting the noise-reduced values obtained under corresponding positive waveform and negative waveform for each pixel;

(S14) converting the noise-reduced values into digitized noise-reduced values; and (S15) mapping the digitized noise-reduced values to corresponding locations of capacitive sensing units.

For a better understanding, a result analysis is illustrated below. After the step S04, the electric potential of the sensing electrode 110 should be $$V_{m1} = (V_{bias1} - V_{well}) + \Delta V_{well\_1} \cdot \left( \frac{C_f}{C_f + C_r + C_p} \right) = 1.5 + 3 \cdot \left( \frac{C_f}{C_f + C_r + C_p} \right).$$

Here, $V_{bias1}$ is the electric potential of the first bias voltage, $V_{well}$ is the well potential, $\Delta V_{well\_1}$ is the change of the well potential caused by a positive waveform (a voltage raise signal) sent by the driving source 160, $C_f$ is a value of the finger capacitance 510, and $(C_r+C_p)$ is a value of the comparative capacitor 170 ($C_p$ is a value of the parasitic capacitance and $C_r$ is a value of the reference capacitor). After the step 505, the first output electric potential can be represented by $$V_1 = V_{m1} \cdot G_f + N = G_f \cdot \left\{ (V_{bias1} - V_{well}) + \Delta V_{well\_1} \cdot \left( \frac{C_f}{C_f + C_r + C_p} \right) \right\} + N.$$

Here, N is the fixed pattern noise caused by the voltage follower circuit and impedance mismatch of circuit elements which results from inaccuracy of the manufacturing process, and $G_f$ is the gain factor of the voltage follower 140, usually less than 1. After the step S09, the electric potential of the sensing electrode 110 should be $$V_{m2} = (V_{bias2} - V_{well}) + \Delta V_{well\_2} \cdot \left( \frac{C_r}{C_f + C_r + C_p} \right) = 1.5 - 3 \cdot \left( \frac{C_r}{C_f + C_r + C_p} \right).$$

After the step S10, the second output electric potential can be represented by $$V_2 = V_{m2} \cdot G_f + N = G_f \cdot \left\{ (V_{bias2} - V_{well}) + \Delta V_{well} \cdot \left( \frac{C_r}{C_f + C_r + C_p} \right) \right\} + N.$$

Here, $V_{bias2}$ is the electric potential of the second bias voltage, $\Delta V_{well\_2}$ is the change of the well potential caused by a negative waveform (a voltage drop signal) sent by the driving source 160. The positive and negative waveforms are symmetric in shape, and are step functions in the present embodiment, i.e. $\Delta V_{well\_1} = -\Delta V_{well\_2} = \Delta V_{well}$. At the final step S12, the output of the differential amplifier 310 can be represented by $$V_{final} = g \cdot (V_1 - V_2) = g \cdot G_f \cdot \left\{ (V_{bias1} - V_{bias2}) + 2\Delta V_{well} \cdot \left( \frac{C_r}{C_f + C_r + C_p} \right) \right\} = g \cdot G_f \cdot 6 \left( \frac{C_r}{C_f + C_r + C_p} \right).$$

Here, g is the gain factor of the differential amplifier 310. The fixed pattern noise term (N) is cancelled in this method.

Figure 8:
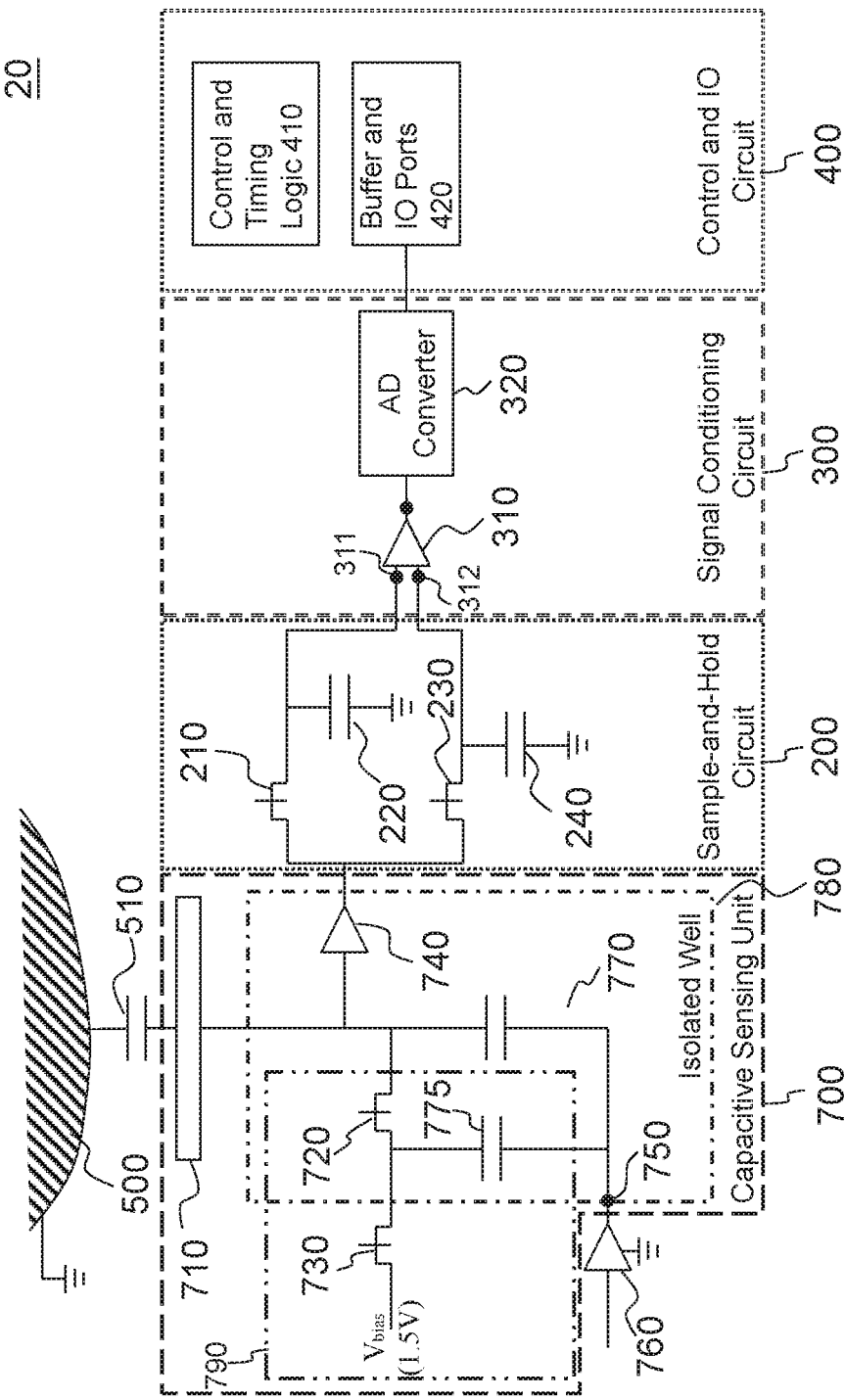
FIG. 8 is an equivalent circuit of the capacitive image sensor (one pixel) of a second embodiment according to the present invention.

Please refer to FIG. 8, FIG. 8 is an equivalent circuit of a second embodiment of the capacitive image sensor 20 (one pixel). The only difference between the present embodiment and the previous embodiment is the capacitive sensing unit 700. More precisely, the bias voltage supply circuit 790 of the capacitive sensing unit 700 is different from the bias voltage supply circuit 190 of the capacitive sensing unit 100. In the present embodiment, the capacitive sensing unit 700 includes an isolated well 780, a sensing electrode 710, a first switch 720, a second switch 730, a voltage follower 740, a well contact 750, a driving source 760, a comparative capacitor 770, and a bias capacitor 775. A parasitic capacitance (not shown) representing the sum of stray capacitance between the sensing electrode 710 and other parts of the capacitive sensing unit 700 that are not connected to it (not shown) can be treated as a part of the comparative capacitor 770. The value of the parasitic capacitance, denoted as $C_p$, may include the parasitic input capacitance of the voltage follower 740, the drain-to-body capacitance of the first switch 720, or the stray capacitance of any device with one node connected to the sensing electrode 710. A reference capacitor (not shown), having a capacitance $C_r$, is formed between the driving source 760 and the sensing electrode 710, and the reference capacitor is used to inject a driving signal to the sensing electrode 710. The comparative capacitor 770 is an equivalent capacitor, denoted as $C_c$, representing the total effect of the parasitic capacitance and the reference capacitor, i.e. $C_c=C_r+C_p$. When a finger 500 approaches the capacitive sensing unit 700, a finger capacitance 510, denoted as $C_f$, is formed therebetween. The sensing electrode 710 is a metal plate at the top side of the capacitive sensing unit 700, used to form one side of a parallel plate capacitor. Here, the parallel plate capacitor is an equivalent capacitor representing the finger capacitance 510. The other side of the parallel plate capacitor is the surface of the finger 500, which is part of the human body. The human body is considered as part of earth ground, or connected to earth ground through a low impedance path. The bias capacitor 775 has a first node and a second node, and the second node of the bias capacitor 775 is connected to the driving source 760. The capacitance of the bias capacitor 775 is much larger than that of the finger capacitance 510 and/or the comparative capacitor 770. The first switch 720 is a MOS device used as a switch to connect or disconnect the first node of the bias capacitor 775 to the sensing electrode 710. The second switch 730 is another MOS device used as a switch to connect or disconnect a bias voltage, denoted as $V_{bias}$, to the first node of the bias capacitor 775. The bias voltage is a 1.5V constant voltage reference in the present embodiment. The voltage follower 740 is a circuit device that has input and output signal. The output signal tracks the input signal. Usually, a voltage follower is implemented as a unity gain amplifier. The input node of the voltage follower 740 is connected to the sensing electrode 710, and the output node is connected to the sample-and-hold circuit 200. The driving source 760 is a low-impedance voltage source to provide a multi-level waveform as the driving signal. The first switch 720, the voltage follower 740, and the comparative capacitor 770 are all formed inside the isolated well 780 (enclosed by a dot-dash frame). The well contact 750 is a contact node for maintaining a well potential of the isolated well 780, and is connected to the output end of the driving source 760. Every node connected to the well contact 750 has the same well potential. Therefore, the components inside the isolated well 780 have their ground potential refer to the well potential. The well potential is equal to the output voltage of the driving source 760. A bias voltage supply circuit 790 (enclosed by a dash-dot-dot frame) is a collective name for the components that controls the supply of the bias voltage to the isolated well 780. The bias voltage supply circuit 790 includes the first switch 720, the second switch 730, and the bias capacitor 775 in the present embodiment. The purpose of the bias voltage supply circuit 790 is to provide different bias voltages to the isolated well 780 at different times.

Figure 9:
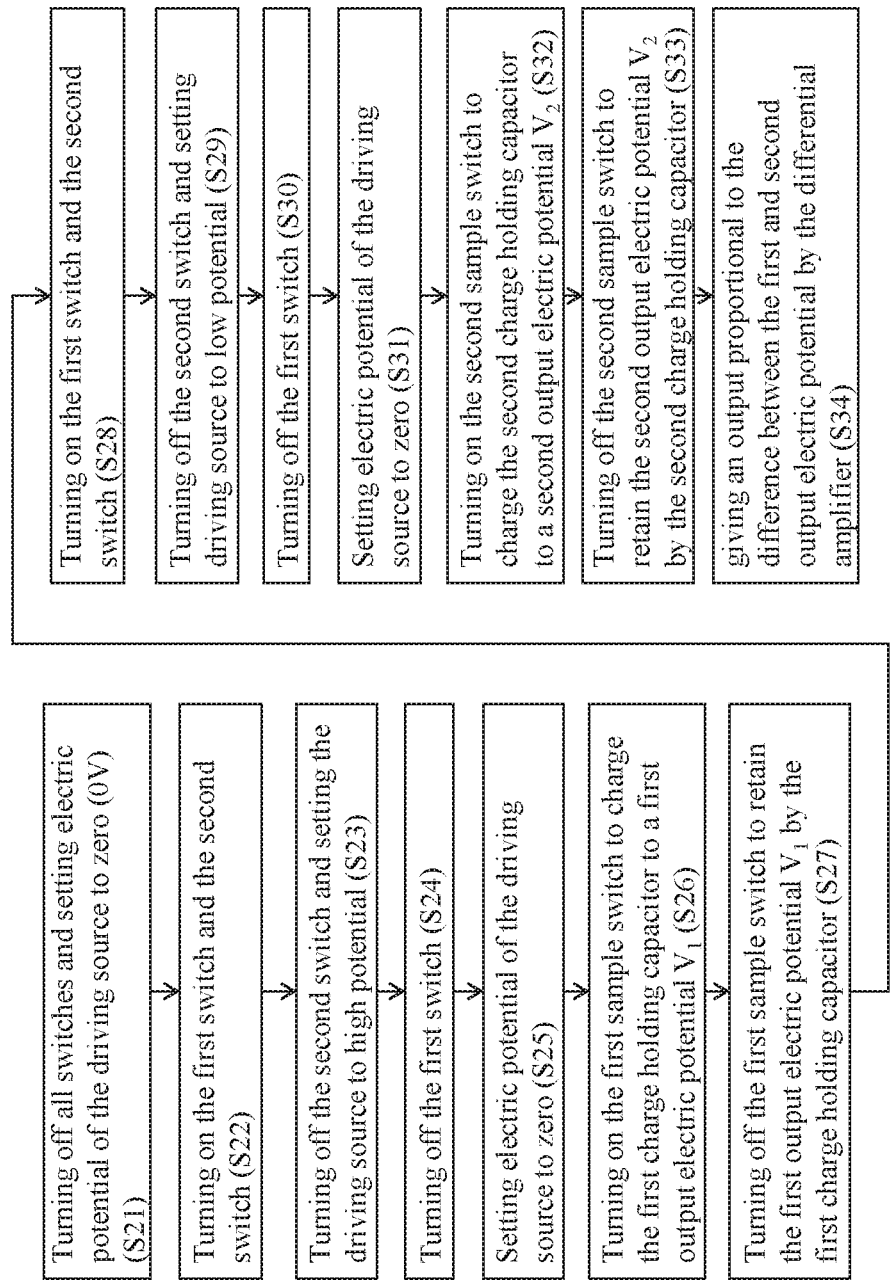
FIG. 9 is a flowchart illustrating a procedure to operate a capacitive sensing unit in the capacitive image sensor of the second embodiment.

A method for operating the capacitive image sensor 20 is also disclosed. Please refer to FIG. 9. It is a flowchart illustrating a procedure to operate a capacitive sensing unit 700 in the capacitive image sensor 20. The steps are:

(S21) turning off all switches (first switch 720, the second switch 730, the first sample switch 210, and the second sample switch 230) and setting the electric potential of the driving source 760 to zero (0V);

(S22) turning on the first switch 720 and the second switch 730 to charge the bias capacitor 775 and the sensing electrode 710 to the bias voltage (1.5V);

(S23) turning off the second switch 730 and setting the driving source 760 to high electric potential (3V) to raise the well potential to the high potential (The potential at the first node of the bias capacitor 775 is now shifted to a voltage about 4.5V, which is equal to the sum of the well potential and the bias voltage. Due to the existence of finger capacitance 510, although much smaller than the capacitance of the bias capacitor 775, the voltage at the first node of the bias capacitor 775 is very close to, not exactly at 4.5V);

(S24) turning off the first switch 720 to disconnect the first node of the bias capacitor 775 from the sensing electrode 710, leaving the metal plate floating and retaining the potential at about 4.5V;

(S25) setting the electric potential of the driving source 760 to zero (0V) to drive the well potential to that of the system ground;

(S26) turning on the first sample switch 210 to charge the first charge holding capacitor 220 to a first output electric potential $V_1$ that tracks the potential of the sensing electrode 710;

(S27) turning off the first sample switch 210 to retain the first output electric potential $V_1$ by the first charge holding capacitor 220;

(S28) turning on the first switch 720 to allow the potential level of the sensing electrode 710 to be the same as that of the first node of the bias capacitor 775 and the second switch 730 to charge the bias capacitor 775 and the sensing electrode 710 to the bias voltage (1.5V);

(S29) turning off the second switch and setting the driving source 760 to low potential (−3V) to drop the well potential to the low potential (The potential at the first node of the bias capacitor 775 is now shifted to a voltage about −1.5V, which is equal to the sum of the well potential and the bias voltage. Due to the existence of finger capacitance 510, although much smaller than the capacitance of the bias capacitor 775, the voltage at the first node of the bias capacitor 775 is very close to, not exactly at −1.5V);

(S30) turning off the first switch 720 to disconnect the first node of the bias capacitor 775 from the sensing electrode 710, leaving the metal plate floating and retaining the potential at about −1.5V;

(S31) setting the electric potential of the driving source 760 to zero (0V) to drive the well potential to that of the system ground;

(S32) turning on the second sample switch 230 to charge the second charge holding capacitor 240 to a second output electric potential $V_2$ that tracks the potential of the sensing electrode 710;

(S33) turning off the second sample switch 230 to retain the second output electric potential $V_2$ by the second charge holding capacitor 240; and (S34) giving an output electric potential proportional to the difference between the first and second output electric potential by the differential amplifier 310.

Here, steps S22 to S24 (S22-S24) are the first reset stage, steps S25 to S27 (S25-S27) are the first sensing stage, steps S28 to S30 (S28-S30) are the second reset stage, steps S31 to S33 (S31-S33) are the second sensing stage, and step S34 is the output stage. The output electric potential proportional to the difference between the first and second output electric potential in step S34 is a noise-reduced value of that pixel (capacitive sensing unit). The noise-reduced value represents a distance between the capacitive sensing unit and the portion surface of the finger above the capacitive sensing unit. The sequence of steps S22-S27 and steps S28-S33 can be exchanged. Namely, a positive waveform and a negative waveform are applied by the driving source to get the noise-reduced value no matter what the sequence is. For a better understanding, take the waveform formed from step S22 to step S25 as a first waveform and the waveform formed from step S28 to step S31 as a second waveform. If the first waveform is a positive waveform, then the second waveform is a negative waveform; if the first waveform is a negative waveform, then the second waveform is a positive waveform. There may be additional steps to convert the output electric potentials into a digitized image. The steps are:

(S35) sequentially collecting the noise-reduced values obtained under corresponding positive waveform and negative waveform for each pixel;

(S36) converting the noise-reduced values into digitized noise-reduced values; and (S37) mapping the digitized noise-reduced values to corresponding locations of capacitive sensing units.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A capacitive image sensor, comprising:
a plurality of capacitive sensing units forming an array, each capacitive sensing unit for transforming a distance between a portion of a surface of an approaching finger and a top surface thereof into an output electric potential, wherein a value of the output electric potential is changed by a driving signal applied to the capacitive sensing unit;

at least one sample-and-hold circuit for capturing and retaining different output electric potentials;

at least one signal conditioning circuit, each comprising at least one differential amplifier for amplifying a difference between two electric potentials retained by the sample-and-hold circuit; and a driving source, for providing the driving signal to the capacitive sensing units, wherein the driving signal is a potential change or potential changes, caused by a positive waveform and/or a negative waveform provided by the driving source; the electric potential at each part of the capacitive sensing units is set to a constant value during reset stages; the difference between two output electric potentials retained in the sample-and-hold circuit is a noise-reduced value representing a distance between the capacitive sensing unit and the portion surface of the finger above the capacitive sensing unit; the sample-and-hold circuit retains at least a first and a second output electric potentials under a corresponding positive waveform or negative waveform; the capacitive image sensor sequentially collects the noise-reduced values under the corresponding positive waveform and negative waveform for each pixel, and maps the noise-reduced values to corresponding locations of the capacitive sensing units to obtain a noise-reduced image of the finger, wherein the capacitive sensing unit further comprises:
a sensing electrode;
a voltage follower, wherein an input node of the voltage follower is connected to the sensing electrode, and an output node of the voltage follower is connected to the sample-and-hold circuit;
a comparative capacitor, wherein one node of the comparative capacitor is electrically connected to the voltage follower, and the other node thereof is electrically connected to the driving source; and
a bias voltage supply circuit, for providing different bias voltages to the sensing electrode, and
wherein the comparative capacitor, a portion of the bias voltage supply circuit, and the voltage follower are MOS devices formed in an isolated well.

2. The capacitive image sensor according to claim 1, wherein shapes of the positive waveform and the negative waveform are symmetric.

3. The capacitive image sensor according to claim 1, wherein the positive waveform or the negative waveform is a step function.

4. The capacitive image sensor according to claim 1, wherein the at least one signal conditioning circuit further comprises an analog-to-digital converter for converting the output electric potentials from the differential amplifier into a digitized value.

5. The capacitive image sensor according to claim 1, wherein the isolated well utilizes deep n-well (DNW) implanted structure.

6. The capacitive image sensor according to claim 1, wherein the comparative capacitor comprises a reference capacitor and parasitic capacitance.

7. The capacitive image sensor according to claim 6, wherein the reference capacitor is a MOSFET (Metal-Oxide-Semiconductor Field-Effect Transistor) capacitor, a PIP (Polysilicon-Insulator-Polysilicon) capacitor or a MIM (Metal-Insulator-Metal) capacitor.

8. The capacitive image sensor according to claim 1, wherein the capacitive image sensor further comprises a control and IO circuit for handling timing sequence and data input/output of the capacitive image sensor.

9. The capacitive image sensor according to claim 1, wherein the sample-and-hold circuit further comprises:
two charge holding capacitors, for holding the output electric potentials sent by the voltage follower; and
at least one selecting switch, for switching between the charge holding capacitors.

10. A method for operating a capacitive image sensor to reduce noise according to claim 1, comprising the steps of:
during a first sensing stage, providing a first measurement to the sample-and-hold circuit while a first input waveform is provided by the driving source;
during a second sensing stage, providing a second measurement to the sample-and-hold circuit while a second input waveform is provided by the driving source;
during an output stage, providing the noise-reduced values by the differential amplifier according to the difference between the first and the second measurements;
sequentially collecting the noise-reduced values obtained under corresponding positive waveform and negative waveform for each pixel;
converting the noise-reduced values into digitized noise-reduced values; and
mapping the digitized noise-reduced values to corresponding locations of capacitive sensing units.

11. The method according to claim 10, wherein if the first waveform is a positive waveform, then the second waveform is a negative waveform; if the first waveform is a negative waveform, then the second waveform is a positive waveform.

* * * * *